_United States Patent_ [19]

Cottman

[11] Patent Number: 4,829,115

[45] Date of Patent: May 9, 1989

[54] ORGANOTHIOETHYL ALCOHOL SEGMERS AS ANTIDEGRADANT SYNERGISTS

[75] Inventor: Kirkwood S. Cottman, Akron, Ohio

[73] Assignee: The Goodyear Tire & Rubber Company, Akron, Ohio

[21] Appl. No.: 163,499

[22] Filed: Mar. 3, 1988

[51] Int. Cl.$^4$ .................. C07C 149/40; C07C 149/20; C08G 63/46; C08K 5/36

[52] U.S. Cl. ..................................... 524/255; 252/48.2; 252/401; 252/404; 252/406; 260/399; 525/347; 524/289; 524/299; 524/302; 524/304; 524/305; 524/310; 524/350; 524/381; 560/9; 560/152; 560/154

[58] Field of Search ............... 524/291, 381, 350, 255, 524/342, 302, 289; 568/55, 46; 525/327.3, 333.2, 350, 437; 252/48.2, 401, 406, 404; 528/376; 560/9, 15, 152, 154; 260/399; 549/528

[56] References Cited

U.S. PATENT DOCUMENTS

| | | |
|---|---|---|
| 2,570,050 | 10/1951 | Eby ........................................ 568/55 |
| 3,025,273 | 3/1962 | Wheelock ............................ 528/376 |
| 3,098,078 | 7/1963 | Druey et al. ........................ 260/399 |
| 3,267,071 | 8/1966 | Schooten et al. ................... 260/399 |
| 3,729,518 | 4/1973 | Lepper et al. ......................... 568/55 |
| 3,879,346 | 4/1975 | Friedrick et al. ................... 524/381 |
| 4,238,575 | 12/1980 | Kleiner et al. ...................... 524/342 |
| 4,486,322 | 12/1984 | Horodysky et al. .................. 568/46 |
| 4,737,300 | 4/1988 | Wirth et al. ........................... 568/46 |

FOREIGN PATENT DOCUMENTS 59-159896 9/1984 Japan ................................... 260/399

_Primary Examiner_—Veronica P. Hoke
_Attorney, Agent, or Firm_—Bruce J. Hendricks

[57] ABSTRACT

This invention is concerned with the stabilization of organic materials subject to oxidative degradation. The synergists of this invention possess organothioethyl alcohol segmers or moieties which enhance the antioxidative activity of phenolic and amine stabilizers. The invention is also concerned with compounds that contain an organothioethyl alcohol moiety and their use in oxidizable materials in combination with polymerizable and/or conventional antidegradants.

11 Claims, No Drawings

ORGANOTHIOETHYL ALCOHOL SEGMERS AS ANTIDEGRADANT SYNERGISTS

TECHNICAL FIELD

This invention is concerned with synergists and to antioxidant systems which employ these synergists. More particularly, this invention relates to organic compositions stabilized against oxidative degradation by a stabilizing system comprising a novel compound possessing or containing an organothioethyl alcohol moiety and phenolic and/or amine antidegradants. It has been discovered that compounds containing a organothioethyl alcohol segmer or moiety can enhance the activity of phenolic and amine antidegradants.

BACKGROUND ART

It is well known that organic materials such as plastics, rubbers, lubricating oils, etc. are prone to oxidation and deterioration in the presence of oxygen. Oxidation of organic materials causes the loss of those intrinsic properties characteristic of the organic material. With a view to preventing deterioration, a variety of antioxidants and antiozonants have been developed; however, these stabilizers fail to prevent completely the deterioration of the desired properties of the materials to which they are added. Thus, those skilled in the art are constantly searching for new and more effective stabilizing systems which are useful for the protection of polymers and other organic materials.

Synergists have been known in the art for some time. See for example U.S. Pat. No. 3,492,336 which discloses use of a tetra-alkyl thioethyl thiodisuccinate with phenolic type antioxidants in the stabilization of polyolefins.

U.S. Pat. No. 4,254,020 discloses compounds such as 2,9-dihydroxy-4,7-dithia-5-methyldecamethylene bis[3-(dodecylthio)propionate]as synergists for phenolic antioxidants.

In U.S. Pat. No. 3,398,116 a thiocarboxylic acid thioether ester is used in combination with a limited group of phenolic antioxidants to stabilize poly-alphaolefins against oxidative degradation.

U.S. Pat. No. 3,758,549 discloses polyalkanol esters of alkylthio-alkanoic acids as synergists with phenolic antioxidants and U.S. Patent Nos. 3,666,716 and 3,505,225 disclose derivatives of diphenylamine and phenylnaphthylamines as antioxidants with dialkyl 3,3'-thiodipropionates as a synergist. U.S. Pat. No. 3,450,671 discloses polyolefin compositions stabilized with dialkyl 3,3'-thiodipropionate and a polyphenol.

An article by R. Chandra, Polymer, Vol. 24, February 1983 discloses styrene-butadiene copolymers stabilized with the antioxidant 3,5-di-t-butyl-4-hydroxybenzylmercaptan and 1,1,5-triphenyl-2-s-(3',5'-di-t-butyl-4'-hydroxy) benzyl-iso-4-thiobiuret as a polymer bound synergist.

U.S. Pat. No. 4,604,417 discloses polymerizable thioester synergists. The compounds of this reference possess a polymerizable moiety which allows for their incorporation into a polymeric network via copolymerization or grafting.

U.S. Pat. No. 3,661,822 discloses a stabilized EPDM polymer which contains 0.75 to 4 parts of a binary synergistic mixture of (A) and (B). (A) is an epoxide selected from the group consisting of: epoxidized soybean oil, epoxidized esters of fatty acids having 10 to 30 carbon atoms, epoxidized straight chain alpha-olefins, epoxidized polybutadiene and diglycidyl ether resin of 4,4'-isopropylidenediphenol; while (B) is an organic sulfide having the formula: R—A—R' wherein A is a radical selected from the group consisting of —S—, —S—S— and —S—R''—S—; R and R' are alkyl, cycloalkyl, aryl, aralkyl, and alkaryl, and R'' is selected from alkylene, arylene, alkylenearylene and heterocyclic divalent radicals. This patent fails to disclose or appreciate that the reaction between a material having epoxy or oxirane groups and a mercaptan will produce a compound that can synergistically enhance the activity of phenolic and amine antidegradants in the stabilization of organic compounds subject to oxidative degradation.

The prior art has suggested that for a compound to exhibit synergistic properties with an antioxidant or antiozonant, it would require a certain amount of mobility of the compound within and about the polymer matrix. The present invention has unexpectedly discovered that high molecular weight synergists can be prepared by reacting a primary, secondary or tertiary mercaptan with a compound that contains at least one epoxy or oxirane group per molecule. Further, it has been discovered that the synergists of this invention demonstrate activity with what is now known in the art as bound antioxidants. This is highly unexpected and contrary to numerous and various teachings in the art.

The synergists of this invention can be produced through the facile reaction of an oil or polymer that possesses oxirane or epoxy groups with a mercaptan. The reaction product thus contains an organothioethyl alcohol moiety or segmer which can synergistically enhance the antidegradative properties of phenolic and amine antioxidants.

The majority of the synergistic stabilizers to date have been used in conjunction with phenolic antioxidants since use with amine antioxidants has not demonstrated synergistic properties. It was felt that synergism was simply overpowered by the excellent stabilizing properties of compounds such as N,N'-dialkyl-p-phenylenediamine. In this regard, it is surprising that the synergists of the instant invention demonstrate synergistic activity with amine type antioxidants. As a result of these discoveries, it has been found that the combined use of the synergists of this invention and an antioxidant brings about an unexpectedly powerful antioxidative effect. None of the cited patents or other literature in the art has disclosed or even suggests the use of the high molecular weight compounds disclosed in this invention as synergists in the stabilization of oxidizable organic materials.

DISCLOSURE OF THE INVENTION

The present invention relates to a stable organic composition which comprises (1) an oxidizable organic material, (2) a phenolic and/or amine antidegradant and (3) an organic compound with a molecular weight of at least 400 that contains at least one moiety of the structural formula:

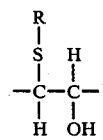

wherein R is selected from primary, secondary or tertiary alkyl radicals of 1–30 carbon atoms, hydroxy substituted alkyl radicals of 2 to 30 carbon atoms, phenyl and substituted phenyl radicals wherein the substituent is an alkyl radical of 1–6 carbon atoms.

There is also disclosed a composition comprising (A) an organic material selected from the group of oxidizable polymers, oils, resins, waxes and fuels; containing an effective amount of a mixture of (B) an antidegradant and (C) a compound with a molecular weight of at least 400 that contains at least one moiety of the structural formula:

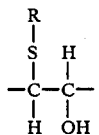

wherein R is selected from primary, secondary or tertiary alkyl radicals of 1–30 carbon atoms, hydroxy substituted alkyl radicals of 2 to 30 carbon atoms, phenyl and substituted phenyl radicals wherein the substituent is an alkyl radical of 1 to 6 carbon atoms.

There is further disclosed a composition of matter that comprises an organic material with a molecular weight of at least 400 which possesses at least one moiety of the structural formula:

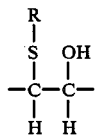

wherein R is selected from primary, secondary or tertiary alkyl radicals of 1–30 carbon atoms, hydroxy substituted alkyl radicals of 2 to 30 carbon atoms, phenyl and substituted phenyl radicals wherein the substituent is an alkyl radical of 1 to 6 carbon atoms.

The present invention also relates to the use of compounds possessing the moiety:

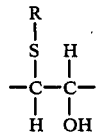

wherein R is as described above; as a synergist with phenolic and amine antidegradants.

The synergists of this invention exhibit their novel properties when combined with a variety of stabilizers known as phenolics and amines, many of which are commercially available and some of which are the subject of patents.

Generally speaking, the synergists of the instant invention contain a β-alkylthioethanol moiety of the structural formula:

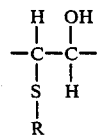

wherein R is a primary, secondary or tertiary alkyl radical of 1 to 30 carbon atoms, hydroxy substituted alkyl radicals of 2 to 30 carbon atoms, phenyl and substituted phenyl radicals wherein the substituent is an alkyl radical of 1 to 6 carbon atoms.

The term segmer or moiety is used in chemistry to mean an indefinite portion of a sample or a molecule.

In general, the synergists of this invention with a molecular weight of at least 400 are prepared by reacting a mercaptan with an epoxidized organic material, such as epoxidized soybean oil, epoxidized polybutadiene or epoxidized linseed oil; in the presence of a base such as KOH or benzyltrimethylammonium hydroxide. After isolation of the synergists of this invention, they are used in conjunction with phenolic and amine antidegradants to lessen or prevent the oxidative degradation of organic materials.

DETAILED DESCRIPTION OF THE INVENTION

Typical of the phenolic antioxidants with stabilizing properties that are improved by the synergists of the present invention are phenolic compounds having the general formula:

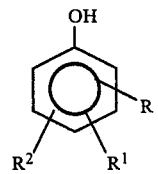

wherein R is a tertiary alkyl radical having 4 to 8 carbon atoms, a cycloalkyl radical having 5 to 12 carbon atoms, or an aralkyl radical having 7 to 12 carbon atoms, and wherein $R^1$ and $R^2$ are alkyl radicals having 1 to 12 carbon atoms, cycloalkyl radicals having 5 to 12 carbon atoms, or aralkyl radicals having 7 to 12 carbon atoms or polyphenolics of the formula:

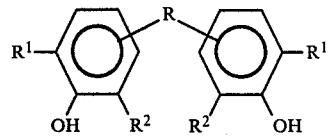

wherein R is divalent radical having 1 to 4 carbon atoms, the group —O—, or the group —S—, and wherein $R^1$ and $R^2$ are alkyl radicals having 1 to 12 carbon atoms, cycloalkyl radicals having 5 to 12 carbon atoms, or aralkyl radicals having 7 to 12 carbon atoms. Preferably at least one of $R^1$ and $R^2$ is a tertiary alkyl radical having 4 to 8 carbon atoms and is in a position ortho to hydroxy group.

Other antioxidants such as:

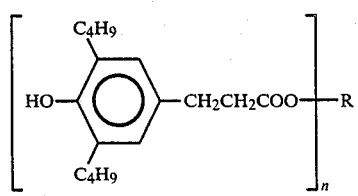

are useful with the synergists of this invention wherein n is an integer from 1 to 4 and R is an alkyl radical having 8 to 20 carbon atoms, an alkylene radical having 2 to 6 carbon atoms, a thiodialkylene radical wherein each alkylene radical has 2 to 6 carbon atoms, a trivalent radical derived from a straight or branched chain hydrocarbon having 3 to 8 carbon atoms, or a tetravalent radical derived from a straight or branched chain hydrocarbon having 1 to 8 carbon atoms.

Representative of the phenolic antioxidants applicable in the present invention include:
2,6-di-tert-butyl-4-methylphenol
2,4,6-tri-tert-butylphenol
2,2'-methylene-bis-(4-methyl-6-tert-butylphenol)
2,2'-thio-bis-(4-methyl-6-tert-butylphenol)
4,4'-thio-bis-(3-methyl-6-tert-butylphenol)
4,4'-butylidene-bis-(6-tert-butyl-3-methylphenol)
Styrenated phenol
Butylated octylated phenol
Butylated-α-methylstyrenated phenol
Styrenated butylated m, p-cresol
4,4'-methylene-bis-(2,6-di-tert-butylphenol)
2,2'-methylene-bis-[4-methyl-6-(1-methylcyclohexy)-phenol]
2,5-diamylhydroquinone
2,6-di-tert-butyl-4-butylthiophenol
Butylated reaction product of p-cresol and dicyclo-pentadiene
Tetrakis[methylene-3-(3,5-di-tert-butyl-4-hydroxyphenyl)propionate]methane
1,3,5-trimethyl-2,4,6-tris-(3,5-di-tert-butyl-4-hydroxybenzyl)benzene
Thiodiethylene-bis-[3-(3,5-di-tert-butyl-4-hydroxyphenyl)propionate]
Octadecyl 3-(3,5-di-tert-butyl-4-hydroxyphenyl) propionate
2,6-bis-(1-phenylethyl)-4-(1-phenylethylthio)phenol Typical of the amine antioxidants with stabilizing properties that are improved by the addition of synergists of the present invention are the naphthylamines, diphenylamine derivatives, quinolines, paraphenylenediamines and the blended amines. A diphenylamine derivative especially useful is the alkylated diphenylamine known as Wingstay TM 29 (The Goodyear Tire & Rubber Company). The quinoline antidegradants are of two types-the polymerized and the nonpolymerized dihydroquinolines and the substituted dihydroquinolines. Numerous paraphenylenediamines have been produced and used as antiozonants and benefit from the use of the synergosts of this invention. Representative examples are Wingstay TM 300 and 100 (products of The Goodyear Tire & Rubber Company), Flexzone TM 3C and 6H (products of Uniroyal, Inc.).

Another class of antidegradant that is useful with the synergists of the instant invention are the polymer bound antidegradants. Most recently, numerous investigators have studied the stabilizing properties of polymers that have as one of their segmeric units, an antioxidant functionality. A more complete discussion of suitable polymeric antidegradants useful with the synergists of the present invention can be found in U.S. Pat. Nos. 3,984,372, 3,962,187, 3,953,402, 3,953,411, 4,097,464, 4,152,319 and 3,658,769.

The synergists of the present invention have as one of their characteristic properties, the ability to vastly improve the effect of numerous compounds which are presently used as antioxidants or antiozonants for organic materials. While the synergists of the present invention may not be considered as stabilizers in their own right, their properties are such that they would be more conventionally classified as "synergists", in that, when combined with known stabilizers, they exhibit the ability to increase stabilization to a degree far exceeding that which would be expected from the additive properties of the individual components.

The compounds of the instant invention may be used with stabilizers (i.e. antioxidants, U.V. absorbers and antiozonants) at a weight ratio of from 1:50 to 50:1 synergist to stabilizer. However, the maximum effectiveness of the stabilizers is usually achieved when a compound of the instant invention is used with a stabilizer at ratios varying from 1:10 to 10:1. The optimum ratio of a given combination varies depending on the organic material to be stabilized, the stabilizers used and the environment to which the organic material is to be exposed. It should be appreciated that one or more synergists of the instant invention may be combined with one or more stabilizers of different types, (i.e. phenolics and amines).

The synergists or the stabilization system according to the present invention (synergist plus stabilizer) can be added to said organic materials in known ways. For instance, it can be combined with the oxidizable organic material either after dilution with a solvent, while in latex form, or directly as is.

The synergists of this invention which possess the β-alkylthioethanol moiety, whether liquid or solid, have a special advantage in that they are not extractable when the mlecular weight of the synergist is sufficient and, therefore, the rubber compositions are highly resistant to aging even after repeated exposure to aqueous detergent solutions or dry cleaning fluids. This lack of extractability is due primarily to the molecular weight of the synergists and to their apparent ability to somehow become less extractable after aging. The synergists of this invention can become polymer bound during vulcanization. It should be understood that the synergists are added to a rubber prior to vulcanization. This feature is especially significant where polymers are used in foam backings for rugs and where polymers are used in solution or latex form to treat fabrics, since such products are often exposed to aqueous detergent solutions or dry cleaning fluids. This feature is also significant where factors such as contact with lubricating oils or exposure to high vacuum conditions are a consideration. The instant invention will also have utility in coating applications such as paints.

The synergists of this invention also may have a plasticizing effect on the polymers that they are added to. Those skilled in the art will readily appreciate the benefits of a plasticizing synergist.

Polymers, oils, resins, polyesters and waxes subject to deterioration that can be conveniently protected by the stabilization system described herein include substituted and unsubstituted, saturated and unsaturated, natural and synthetic polymers, oils, fuels and waxes. The oxidizable natural polymers include natural rubber in its various forms, e.g., pale crepe and smoked sheet, and balata and gutta percha. The oxidizable synthetic polymers are prepared from a single monomer (homopolymer) or a mixture of two or more copolymerizable monomers (copolymer) wherein the monomers are combined in a random distribution or block form. The monomers may be substituted or unsubstituted and may possess one or more double bonds, for example, diene monomers, both conjugated and nonconjugated, and monoolefins including cyclic and acyclic monoolefins, especially vinyl and vinylidene monomers. Examples of conjugated dienes are 1,3-butadiene, isoprene, chloroprene, 2-ethyl-1,3-butadiene, 2,3-dimethyl-1,3-butadiene and piperylene. Examples of nonconjugated dienes are 1,4-pentadiene, 1,4-hexadiene, 1,5-hexadiene, dicyclopentadiene, 1,5-cyclooctadiene and ethylidene norbornene. Examples of acyclic monoolefins are ethylene, propylene, 1-butene, isobutylene, 1-pentene and 1-hexene. Examples of cyclic monoolefins are cyclopentene, cyclohexene, cyclooctene and 4-methyl-cyclooctene. Examples of vinyl monomers are styrene, acrylonitrile, acrylic acid, ethylacrylate, vinyl chloride, butylacrylate, methyl vinyl ether, vinyl acetate and vinyl pyridine. Examples of vinylidene monomers are α-methylstyrene, methacrylic acid, methyl methacrylate, itaconic acid, ethyl methacrylate, glycidyl methacrylate and vinylidene chloride. Representative examples of the synthetic polymers are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene or acrylonitrile; butyl rubber, which is a polymerization product of a major proportion of a monoolefin and a minor proportion of a multiolefin such as butadiene or isoprene: polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1.4-hexadiene, ethylidene norbornene and methylene norbornene and polyester.

It has been found that addition of the synergist and the stabilizer (stabilization system) to organic materials in the range from 0.01 to 10.0 parts per hundred of organic material by weight will effectively protect the organic material from deterioration. As described above, the stabilization system according to the present invention comprises the novel compounds possessing the β-alkylthioethanol moiety in combination with a known stabilizer. The stabilization system of the present invention demonstrates activity superior to that of most conventional systems prepared by combining two or more commercial stabilizers.

BEST MODE FOR CARRYING OUT THE INVENTION

Preparation of Synergists

The novel compounds of this invention are prepared by reacting a compound containing an epoxy group also known as an oxirane group having the formula:

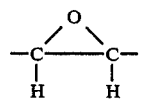

with a primary, secondary, or tertiary mercaptan of 1-30 carbon atoms, or a hydroxy substituted mercaptan of 2-30 carbon atoms or an aromatic mercaptan of 6-12 carbon atoms.

The epoxidized compounds that are useful starting materials to produce the synergists of this invention include epoxidized soybean oil, peanut oil, tung oil, corn oil, beef tallow, linseed oil, fish oils, fats, esters and polyesters. Also useful are the epoxidized pine oils, pine resins and epoxidized polymers that are derived from styrene butadiene copolymers, nitrile-butadiene resins and acrylonitrile-butadiene-styrene resins, natural rubber, polyisobutylene, polybutadiene, polyisoprene and the like. These starting materials which possess the oxirane or epoxy moiety are reacted with primary, secondary and tertiary mercaptans. The alkyl radical of the mercaptan may contain from 1 to 30 carbon atoms, preferably from 1-20 carbon atoms and most preferably from 8 to 14 carbon atoms. It must be remembered that the molecular weight of the epoxy-mercaptan adduct exceed 400.

Preparation of the epoxy compound starting material is accomplished using known procedures in the art and does not form a part of this invention. The formation of epoxy groups on unsaturated hydrocarbon macromolecules, particularly elastomers such as polybutadiene and polyisoprenes, is well known. For example, U.K. Pat. No. 1,083,316 discloses a method for the epoxidation of unsaturated macromolecular substances, comprising reacting an aqueous suspension of said substance with an aromatic peracid.

The synergists of this invention are preferably prepared using epoxidized soybean oil, linseed oil, and epoxy alpha-olefins. Various epoxidized soybean oils are available commercially, as represented by such products as Paraplex G-50, G-61, and G-62, and Flexol EPO. Epoxidized higher fatty acid esters are typified by esters of fatty acids having 10 to 30 carbon atoms in the chain with alkanols having up to 10 carbon atoms (e.g., methyl alcohol, octyl alcohol, decyl alcohol, glycerol and the like). They are represented by such commercial materials as Drapex 3.2 (octyl epoxy stearate having a molecular weight of 410) or Monopolex-71 (an epoxidized oleate ester with an average molecular weight of 380). The epoxy alpha-olefins are usually made by treating a straight chain alpha-olefin with oxygen under pressure in the presence of a catalyst such as molybdenum carbonyl or molybdenum naphthenate. An important epoxide of a diolefin homopolymer is epoxidized polybutadiene, as represented by the commercial material known as "Oxiron" containing 10% epoxy, iodine number 185, viscosity 1800 poises at 25° C. (see U.S. Pat. No. 2,829,135). Epoxide contents in such materials frequently run from 2% to above 25%. The epoxy resins which are diglycidyl ether types of bisphenol A (4,4'-isopropylidenediphenol) are usually made in a known manner by reacting bisphenol A with epichlorohydrin. Commercial examples are Epon 820, Epon 826, Epon 828, Epon 830 and similar types which usually have an epoxy equivalent of 125 to 4000 and a viscosity in the range of from 100 to 59,000 centipoises at 25° C.

The following is a more specific reaction scheme for compounds of the invention and certain control or comparative compounds. All parts are parts by weight unless otherwise noted.

EXAMPLE 1

Preparation of Epoxidized Polybutadiene 220 g of a low molecular weight 1,4-polybutadiene of approximately 5,000 molecular weight was placed in a 2 liter flask and 53 g of formic acid, 40 ml of tetrahydrofuran and 40 g of hexane were charged to the reaction vessel. 69 g of hydrogen peroxide was then added. The mixture was reacted at 35° C. for about 1 hour, at 45° C. for 1 hour and then at 55° C. for 1 additional hour. The product was neutralized with 400 g of dry sodium carbonate and diluted with 200 ml of additional hexane. The reaction mixture was then filtered and an additional charge of sodium carbonate and sodium sulfate were added to dry the product solution. The product was distilled under vacuum to a pot temperature of 55° C. at 15 mm of mercury to remove the solvents. The isolated product weighed 255 g and NMR analysis showed the product contained 4 weight percent 1,2-polybutadiene, 65 weight percent 1,4-polybutadiene, and 31 weight percent epoxidized polybutadiene.

EXAMPLE 2

Preparation of Synergist 20 g of the polymer prepared in Example 1 and 25 g of dodecanethiol were charged to a flask containing 0.07 g of potassium hydroxide powder. The mixture was heated for 1 hour at 145° to 155° C. The reaction mixture was poured into an extraction thimble and continuously extracted with hot methanol for 24 hours. The methanol was distilled away from the functionalized polymer. The dried polymer was found to contain 7.8 weight percent sulfur. This product thus contained 44.6 parts of bound dodecanethiol which forms part of the β-alkylthioethanol moiety. When considered as percent moiety, the product contained about 59 weight percent of the β-alkylthioethanol moiety.

EXAMPLE 3

Preparation of Synergist 20 g of SBR (cold polymerization 23.5% styrene by weight) with a Mooney viscosity of 50 containing 10 weight percent epoxidation was dissolved in 275 g of orthodichlorobenzene. 9 g of n-dodecanethiol and 0.5 g of potassium hydroxide powder were charged to the reaction vessel. The contents of the flask were reacted at 145° C. for 1¼ The product was stripped to remove 205 g of solvent and then poured into a extraction thimble. The product was continuously extracted for 30 hours with hot methanol (boiling point of methanol). The isolated and dried polymer was found to contain 2.9% sulfur by weight and thus, the polymer contained 18.3 parts of bound dodecanethiol or 21.8 parts by weight of the β-alkylthioethanol moiety.

EXAMPLE 4

Evaluation of Synergist From Example 2

The polymeric synergist prepared in Example 2 was evaluated as an antioxidant synergist in combination with Wingstay TM C, a commercially available antioxidant from The Goodyear Tire & Rubber Company, which consists primarily of butylated di-(dimethylbenzyl)phenol. 0.034 g of the polymeric synergist from Example 2 which contains 0.02 g of the β-alkylthioethanol moiety was dissolved in SBR (a styrene butadiene copolymer, hot polymerization with 23.5% styrene content) toluene cement containing 3 g of SBR. The cement thus contained 1.13 parts of the polymeric synergist or 0.667 parts of the β-alklylthioethanol moiety or 0.5 parts of bound dodecanethiol. As a matter of convenience, the inventor herein used the amount of bound mercaptan as the measure of active component. To the sample was added 0.015 g of Wingstay TM C (0.5 parts). The polymer solution was cast on aluminum foil dried and evaluated by the oxygen absorption test at 100° C. Control samples containing only the synergist and only the antioxidant were also prepared. The testing procedure is the type described in detail in Industrial and Engineering Chemistry, Vol. 43, page 456, 1951 and Industrial and Engineering Chemistry, Vol. 45, page 392, 1953. The data obtained from this evaluation are found in Table I.

TABLE I

| Sample No. | Stabilizer System | Hours to Absorb 1.0% $O_2$ by wt at 100° C. |
|---|---|---|
| I | 1.13 pt compound from Ex. 2** | 7 |
| II | 0.5 pt Wingstay TM C* | 162 |
| III | 1.0 pt Wingstay TM C | 246 |
| IV | 1.13 pt compound from Ex. 2 and 0.5 pt Wingstay TM C | 655 |

*Wingstay TM C - butylated di-(dimethylbenzyl)phenol.
**1.13 pt of compound from Ex. 2 contains 0.5 parts of bound dodecanethiol.

As demonstrated in Table I, the use of the polymeric synergist from Example 2 alone provided little or no protection from oxidative degradation (Sample No. I). In like fashion 0.5 and 1.0 part of Wingstay TM C provided only moderate protection (Samples Nos. II and III). In contrast, combining the synergist from Example 2 with 0.5 part of Wingstay TM C results in over 655 hours of protection.

Sample No. IV was also evaluated to oxygen absorption levels of 2 and 3%. Sample No. IV required 1002 hours to absorb 2% $O_2$ and 1150 hours to 3% $O_2$ by weight.

EXAMPLE 5

Preparation of Synergist

To a reaction flask was charged 5 g of an NBR polymer containing 5 mole percent epoxidation, 5 g of n-dodecanethiol, 0.14 g of potassium tertiary butoxide and 50 g of methylisobutyl ketone (MIBK). The reaction flask was placed in a circulating water bath for 17 hours at 50° C. The MIBK solvent was then evaporated from the product and the dried polymeric synergist was extracted 24 hours with hot isopropyl alcohol. The dried synergist was found to contain 1.44% sulfur by weight and therefore, the epoxidized NBR polymer contained about 11% by weight of the β-alklylthioethanol moiety or 9.09 parts of bound dodecanethiol per 100 parts of the functionalized polymer.

EXAMPLE 6

Preparation of Synergist 50 g of natural rubber containing 50% epoxidation was dissolved in 500 ml of xylene. The solution was placed in a 2 liter flask containing 1 gram of sodium carbonate to neutralized residual acid from the epoxidation. Then 0.8 g of potassium hydroxide, 0.4 g of potassium tertiary butoxide (as a co-catalyst) and 22 g of 1-dodecanethiol were charged to the vessel. The reaction mixture was heated to 130° C. for 6 hours. During this time, thin layer chromatography indicated that the dodecanethiol was reacting. Most of the dodecanethiol reacted by adding across the epoxide polymer groups while a small amount oxidized to the disulfide. The product solution was poured onto a Teflon tray to dry and the dried polymeric synergist was extracted for 48 hours with hot methanol. A chemical analysis of the unextracted synergist indicated 5.3% sulfur by weight. Analysis of the extracted synergist showed 3.0% sulfur which translates into 22.5% of the β-alkylthioethanol moiety by weight or 18.9 parts of the bound dodecanethiol.

EXAMPLE 7

Preparation of Synergist 50 g of 1-dodecanethiol, 150 g of epoxidized soybean oil with 6.8% minimum oxirane oxygen content by weight (Paraplex ™ G-62 by the C.P. Hall Company) and 0.71 g of potassium hydroxide powder were reacted under a nitrogen blanket for 1 hour at ambient temperature and at 175° C. for 3 hours.

The product was isolated and analyzed. Gas chromatography indicated no unreacted thiol in the reaction mixture. Gel permeation chromatography also indicated that 100% of the thiol had reacted.

EXAMPLE 8

Preparation of Synergist 300 g of epoxidized soybean oil (Paraplex ™ G62), 100 g of 1-dodecanethiol and 1 g of potassium hydroxide powder were heated under nitrogen to 170° C. and reacted for 30 minutes. Gas chromatography of the reaction mixture indicated that all of the thiol had reacted with the epoxidized oil, thus providing 100% yield.

EXAMPLE 9

Evaluation of Synergist

The synergist prepared in Example 8 was evaluated as an antioxidant synergist. It was evaluated using the indicated parts in combination with a masterbatch polymeric antioxidant (polymer bound antioxidant). The polymeric antioxidant was a copolymer of butadiene and the polymerizable antioxidant monomer N-(4-anilinophenyl)methacrylamide. The antioxidant copolymer was prepared using a process similar to that described and claimed in U.S. Pat. No. 4,521,574. The antioxidant polymer contained 35% by weight of segmers derived from N-(4-anilinophenyl)methacrylamide with the balance being 1,3-butadiene segmers. The antioxidant system was evaluated at 100° C. in SBR by the oxygen absorption test. The data from this evaluation is contained in Table II.

TABLE II

| Sample No. | Stabilizer System | Hours to Absorb 1.0% $O_2$ by wt at 100° C. |
|---|---|---|
| V | 0.5 pt of bound ddt** from Ex. 8 | 22 |
| VI | 0.5 pt polymeric antioxidant* | 251 |
| VII | 0.5 pt of bound ddt from Ex. 8 and 0.5 pt polymeric antioxidant | 553 |
| VIII | 1.0 pt polymeric antioxidant | 448 |
| Control | 3.0 pt of Paraplex-G-62 | 5 |

*polymeric antioxidant - a copolymer consisting of 65 parts butadiene and 35 parts of N—(4-anilinophenyl) methacrylamide.
**ddt = dodecanethiol As clearly demonstrated, the use of a synergist according to this invention at 0.5 part level of bound dodecanethiol in combination with the polymeric antioxidant dramatically increases the number of hours to 1.0% $O_2$ over the use of 1 part of the polymeric antioxidant alone by about 25%. This is an unexpected and nonobvious result.

EXAMPLE 10

Evaluation of Synergists

The procedure of Example 9 was used except that the synergist prepared in Example 2 was evaluated with the polymeric antioxidant. Table III sets out the amount of each component and the hours to 1% $O_2$ by weight.

TABLE III

| Sample No. | Stabilizer System | Hours to 1% $O_2$ |
|---|---|---|
| IX | 0.5 pt. polymeric antidegradant* | 251 |
| X | 0.5 pt of bound ddt from Ex. 2 | 7 |
| XI | 0.5 pt. polymeric antidegradant and 0.5 pt bound ddt from Ex. 2 | 429 |
| XII | 0.25 pt. polymeric antidegradant and 0.75 pt of bound ddt from Ex. 2 | 448 |

*polymeric antioxidant - a copolymer consisting of 65 parts butadiene and 35 parts of N—(4-anilinophenyl) methacrylamide.

This data indicates that a small amount of a polymeric antidegradant in combination with a synergist of this invention will provide protection that is 75% better than the polymeric antidegradant alone at the 0.5 part level (Sample XII vs. IX).

EXAMPLE 11

Isomeric Mercaptans

The procedure described in Example 7 to produce the synergists was used except that secondary (Example 11A) and tertiary (Example 11B) dodecanethiol were substituted for the 1-dodecanethiol. The synergists were isolated and then evaluated with Wingstay ™ C using the procedure described in Example 4. Table IV sets forth the hours to 1, 2 and 3% $O_2$. This test was conducted to further demonstrate the effectiveness of the synergists of this invention since many antidegradants alone become auto-oxidative after about 1% $O_2$ uptake. Auto-oxidative means that the number of hours between 1% and 2% is much less than the number of hours to 1%. This phenomena can become especially important when large rubber articles (i.e. truck tires) have service lifetimes of from 3 to 10 years.

TABLE IV

| Sample No. | Stabilizer System | Hours to 1% | 2% | 3% |
|---|---|---|---|---|
| XIII | 0.5 pt. of bound sec-ddt from Ex. 11 A (Control) | 67 | 110 | 130 |
| XIV | 0.5 pt. of bound tert-ddt from Ex. 11 B (Control) | 43 | 61 | 75 |
| XV | 0.5 pt. of bound ddt from Ex. 7 and 0.5 pt. of Wingstay ™ C | 1018 | 1617 | 1936 |
| XVI | 0.5 pt. of bound sec-ddt from Ex. 11A and 0.5 pt. of Wingstay ™ C | 1210 | 1717 | 2104 |
| XVII | 0.5 pt. of bound tert-ddt from Ex. 11B and 0.5 pt. of Wingstay ™ C | 931 | 1394 | 1530 |
| XVIII (A) | 0.5 pt. of Wingstay ™ C (Control) | 227 | 248 | 260 |
| XVIII (B) | 1.0 pt. of Wingstay ™ C (Control) | 311 | 386 | 420 |

The results amply demonstrate that the synergists of this invention, secondary and tertiary mercaptans also lessen the auto-oxidative phenomenon.

EXAMPLE 12

Amine Antioxidants

To test the effectiveness of the synergists of this invention with amine antidegradants, the synergist prepared in Example 8 was evaluated in SBR in combination with Wingstay ™ 29, which is styrenated diphenylamine, a product of The Goodyear Tire & Rubber Company. The procedure described in Example 4 was used and the results are set out in Table V.

TABLE V

| Sample No. | Stabilizer system | Hours to | | |
|---|---|---|---|---|
| | | 1% | 2% | 3% |
| XIX | 0.1 pt. of Wingstay TM 29 (Control) | 48 | 63 | 75 |
| XX | 0.5 pt. of bound ddt from Ex. 8 and 0.1 pt. of Wingstay TM 29 | 998 | 1574 | 1689 |
| Control | 0.5 pt of bound ddt | 48 | 75 | 99 |

This information amply demonstrates the powerful nature of the synergists of this invention when combined with amine antioxidants.

EXAMPLE 13

Antiozonants

To evaluate the effectiveness of the synergists with an antiozonant, the product from Example 8 was evaluated with Santoflex 13 manufactured by Monsanto which is N-1,3-dimethylbutyl-N'-phenyl-p-phenylenediamine. Oxygen absorption to 1, 2 and 3% in SBR was determined as in Example 4 and the results are set out in Table VI.

TABLE VI

| Sample No. | Stabilizer System | Hours to | | |
|---|---|---|---|---|
| | | 1% | 2% | 3% |
| XXI | 0.1 pt. Stanoflex 13 (Control) | 394 | 421 | 432 |
| XXII | 0.1 pt. Stanoflex 13 plus 0.5 pt. of bound ddt from Ex. 8 | 620 | 851 | 946 |
| XXIII | 0.1 pt. Epoxidized Soybean Oil (Paraplex TM G-62- Control) | 5 | 9 | 13 |
| Control | 0.5 pt. of bound ddt (Control) | 48 | 75 | 99 |

The data from Table VI demonstrate that synergists of this invention are capable of greatly enhancing the activity of a commercially accepted antiozonant.

EXAMPLE 14

Use of a Low Molecular Weight Mercaptan in Preparation of a Synergist

Into a 250 ml flask was added 88 g of epoxidized soybean oil (EPSBO) (Paraplex TM G-62), 30 g of 2-mercaptoethanol and 0.79 g KOH powder. The flask contents were stirred at 150° C. for 90 minutes. Gas chromatography indicated that all of the 2-mercaptoethanol had reacted. The product did not have the foul 2-mercaptoethanol odor. The yield was quantitative.

EXAMPLE 15

Into a 250 ml flask was added 75 g of EPSBO (Paraplex TM G-62), 25 g of 3-mercaptopropionic acid and 0.70 g of KOH powder. The flask contents were reacted at 165° C. for 75 minutes. Gas Chromatography indicated that there was no unreacted 3-mercaptopropionic acid in the flask. The yield was quantitative.

EXAMPLE 16

Use of an Aromatic Mercaptan

Into a 250 ml flask was charged 75 g of EPSBO (Paraplex TM G-62) and 0.5 g of KOH powder. Thiophenol was added at 90° C. and then the flask contents were further heated. Five minutes later the temperature had rapidly increased to 174° C. as the product color instaneously changed from amber to dark brown. Gas chromatography, after 20 minutes of reaction, showed a trace of unreacted thiophenol. The reactor temperature was maintained at 162° C. The total reaction time was 60 minutes. Gas chromatography then indicated that there was no unreacted thiophenol in the product.

EXAMPLE 17

Use of a Tetradecyl Mercaptan Into a 250 ml flask was weighed 75 g of EPSBO (Paraplex TM G-62), 0.5 g KOH powder and 28 g of normal tetradecyl mercaptan. The flask contents were reacted at 180° C. for 42 minutes. Gas chromatography indicated that all of the mercaptan had reacted with the EPSBO to form the synergist.

EXAMPLE 18

Low Molecular Weight Epoxidized Polybutadiene 20 g of a low molecular weight liquid epoxidized polybutadiene polymer (25 weight percent epoxy content) was weighed into a reactor with 0.16 g KOH powder and 2.2 g of thiophenol. The reactor contents were reacted under nitrogen at 152° C. for 95 minutes. The product turned dark brown as it reacted. The synergist was formed as the thiophenol reacted across the epoxide groups of the polymer. The polymer was found to contain 2.48% sulfur.

EXAMPLE 19

Preparation of a Polymer Bound Antioxidant

Into a reactor was weighed 200 g of EPSBO (Paraplex TM G-62), 67.5 g of 2,2'-methylenebis(4-methyl-6-tert.butylphenol) [AO 2246] and 0.55 g of KOH powder. The reactor contents were reacted under a nitrogen blanket between 190° and 200° C. for 4½ hours. Thin layer chromatography, gas chromatography and gel permeation chromatography all indicated that the phenolic antioxidant had reacted across the epoxy sites.

EXAMPLE 20

Preparation of Bound Antioxidant and Bound Synergist

Into a reactor was weighed 100 g of EPSBO (Paraplex TM G-62), 17 g 2,2'-methylene-bis-(4-methyl-6-tert.butylphenol) hereinafter referred to as A02246 and 0.5 g of KOH powder. The reactants were stirred at 170° C. for 30 minutes and then 17 g of 1-dodecanethiol was added. The reaction was followed by gas chromatography for 4 hours until all of the A02246 and 1-dodecanethiol had disappeared through reaction with the epoxide sites. The yield was quantitative.

EXAMPLE 21

Evaluation of Materials

The products produced in Examples 14–20 were evaluated using the procedure set out in Example 4 and the results are set forth in Table VII.

TABLE VII

| Sample No. | Stabilizer System | Hours to | | |
|---|---|---|---|---|
| | | 1% | 2% | 3% |
| XXIV | 0.5 pt. of bound mercaptoethanol from Ex. 14 | 4 | 9 | 13 |
| XXV | 0.5 pt. of bound mercaptoethanol from Ex. 14 and 0.5 pt. of Wingstay TM C | 836 | 1275 | 1381 |
| XXVI | 0.5 pt. of bound 3-mercaptopropionic acid from Ex. 15 | 5 | 9 | 14 |
| XXVII | 0.5 pt. of bound 3-mercapto | 516 | 599 | 665 |

TABLE VII-continued

| Sample No. | Stabilizer System | Hours to 1% | 2% | 3% |
|---|---|---|---|---|
| | propionic acid from Ex. 15 and 0.5 pt of Wingstay ™ C | | | |
| XXVIII | 0.5 pt of bound A02246* from Ex. 19 | 371 | 527 | 583 |
| XXIX | 1.0 pt of bound A02246* from Ex. 19 | 540 | 818 | 960 |
| XXX | 0.5 pt of bound A02246* from Ex. 19 and 0.5 pt of bound ddt from Ex. 8 | 1070 | 2135 | —** |
| XXXI | 0.5 pt of bound A02246* and 0.5 pt of bound ddt from Ex. 20 | 1270 | 2376 | —** |

*2,2'-methylene-bis-(4-methyl-6-tert.butylphenol).
**Test was terminated before 3% O₂ was absorbed.

Industrial Applicability

From the data obtained, it is evident that the synergists disclosed herein significantly enhance the stability of polymers when combined with known antidegradants. The industrial applications are readily apparent in light of the exceptional synergistic activity of these compounds. Use of the synergists of this invention can significantly reduce the amount of costly antioxidant that is needed to provide the desired stability to the organic material.

While certain representative embodiments and details have been shown for the purpose of illustrating the invention, it will be apparent to those skilled in this art that various changes and modifications may be made herein without departing from the scope of this invention.

I claim:

1. A stable organic composition which comprises (1) an oxidizable organic material, (2) a phenolic and/or amine antidegradant and (3) a synergist which enhances the activity of said antidegradant wherein said synergist has a molecular weight of at least 400 and contains at least one moiety of the structural formula:

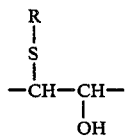

wherein R is selected from primary, secondary or tertiary alkyl radicals of 1 to 30 carbon atoms, hydroxy substituted alkyl radicals of 2 to 30 carbon atoms, phenyl and substituted phenyl radicals wherein the substituent is an alkyl radical of 1 to 6 carbon atoms and said synergist is prepared by reacting a mercaptan with an epoxidized organic material selected from the group consisting of soybean oil, peanut oil, tung oil, corn oil, beef tallow, linseed oil, fish oils, polyesters, fats, styrene butadiene copolymer, nitrile-butadiene resins, acrylonitrile-butadiene-styrene resin, natural rubber, polyisobutylene, polybutadiene and polyisoprene.

2. The stable organic composition of claim 1 wherein the oxidizable organic material is selected from the group comprising oils, resins, waxes, natural rubber, polychloroprene, polyisoprene, polybutadiene, copolymers of isoprene and butadiene, copolymers of styrene and butadiene, butyl rubber, polyurethanes, polyethylene, polypropylene, ethylene propylene copolymers, terpolymers of ethylene propylene and a conjugated diene, polyesters and terpolymers of styrene butadiene and acrylonitrile and terpolymers of styrene butadiene and isoprene.

3. The stable organic composition of claim 1 wherein the antidegradant is selected from the group comprising butylated di-(dimethylbenzyl)phenol, polymers having segmers derived from N-(4-anilinophenyl)methacrylamide; styrenated diphenylamine, N-1,3-dimethylbutyl-N'-phenyl-p-phenylenediamine, styrenated phenol, 2,2'-methylene-bis-(4-methyl-6-tert-butylphenol), styrenated butylated m, p-cresol, naphthylamine, quinolines and tetrakis[methylene 3-(3,5-di-tert-butyl-4-hydroxyphenyl)propionate]methane.

4. A composition according to claim 2 wherein the oxidizable organic material is a vulcanizable polymer and the polymer is vulcanized.

5. The stable organic composition of claim 1 wherein the weight ratio of said synergist to said antidegradant is from 1:50 to 50:1.

6. A method for enhancing the stabilizing activity of an amine and/or phenolic stabilizer comprising using in combination with said stabilizer a synergist with a molecular weight of at least 400 and possessing the moiety:

$$\begin{array}{c} R \\ | \\ S \quad H \\ | \quad | \\ -C-C- \\ | \quad | \\ H \quad OH \end{array}$$

wherein R is selected from primary, secondary or tertiary alkyl radicals of 1 to 30 carbon atoms, hydroxy substituted alkyl radicals of 2 to 30 carbon atoms, phenyl and substituted phenyl radicals wherein the substituent is an alkyl radical of 1 to 6 carbon atoms; and wherein said synergist is prepared by reacting a mercaptan with an epoxidized material selected from the group consisting of soybean oil, peanut oil, tung oil, corn oil, beef tallow, linseed oil, fish oils, polyesters, fats, styrene butadiene copolymer, nitrile-butadiene resins, acrylonitrile-butadiene-styrene resin, natural rubber, polyisobutylene, polybutadiene and polyisoprene.

7. The method of claim 6 wherein the weight ratio of synergist to stabilizer is from 1:50 to 50:1.

8. A synergist that enhances the activity of a pahenolic and/or amine antidegradant comprising an organic material with a molecular weight of at least 400 which possesses at least one moiety of the structural formula:

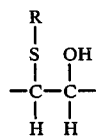

wherein R is selected from primary, secondary or tertiary alkyl radiclas of 1 to 30 carbon atoms, hydroxy substituted alkyl radicals of 2 to 30 carbon atoms, phenyl and substituted phenyl radicals wherein the substituent is an alkyl radical of 1 to 6 carbon atoms and said synergist is prepared by reacting a mercaptan with an epoxidized organic material selected from the group consisting of soybean oil, peanut oil, tung oil, corn oil, beef tallow, linseed oil, fish oils, polyesters and fats.

9. A composition of matter according to claim 8 wherein R is selected from primary, secondary or tertiary alkyl radicals of 9 to 20 carbon atoms and phenyl radicals.

10. A compoistion of matter according to claim 9 wherein R is selected from alkyl radicals of 10 to 14 carbon atoms and phenyl radicals.

11. A composition of matter according to claim 8 which is in physical admixture with an antidegradant.

* * * * *